United States Patent
Choppin et al.

(10) Patent No.: US 7,288,258 B2
(45) Date of Patent: Oct. 30, 2007

(54) POLYEPITOPIC PROTEIN FRAGMENTS OF THE E6 AND E7 PROTEINS OF HPV, THEIR PRODUCTION AND THEIR USE PARTICULARLY IN VACCINATION

(75) Inventors: Jeannine Choppin, Rosny-sous-Bois (FR); Isabelle Bourgault Villada, Paris (FR); Jean-Gerard Guillet, Paris (FR); Francine Connan, Deuil la Barre (FR); Estelle Ferries, Paris (FR)

(73) Assignees: Peptide Immune Ligands, Labege (FR); Institut National de la Sante et de la Recherche Medicale INSERM, Paris (FR)

( * ) Notice: Subject to any disclaimer, the term of this patent is extended or adjusted under 35 U.S.C. 154(b) by 368 days.

(21) Appl. No.: 10/858,384

(22) Filed: Jun. 2, 2004

(65) Prior Publication Data

US 2005/0033025 A1    Feb. 10, 2005

Related U.S. Application Data

(62) Division of application No. 09/980,523, filed as application No. PCT/FR00/01513 on May 31, 2000, now Pat. No. 6,783,763.

(30) Foreign Application Priority Data

Jun. 3, 1999    (FR) .................................. 99 07012

(51) Int. Cl.
A16K 39/12    (2006.01)
(52) U.S. Cl. ................. 424/204.1; 530/300; 536/23.72
(58) Field of Classification Search ............. 424/204.1, 424/186.1; 530/300; 536/23.72
See application file for complete search history.

(56) References Cited

U.S. PATENT DOCUMENTS 5,932,412 A    8/1999    Dillner et al.

2003/0099634 A1    5/2003    Vitiello et al.

FOREIGN PATENT DOCUMENTS

| EP | 0 451 550 | 10/1991 |
| EP | 0 523 391 | 1/1993 |
| EP | 0 728 764 | 8/1996 |
| WO | WO93/22338 | 11/1993 |
| WO | WO98/23635 | 6/1998 |

OTHER PUBLICATIONS

Barbosa et al. The EMBO Journal, 1990, vol. 9, No. 1, pp. 153-160.*
By Beatrice Culmann et al., "identification of multirestricted immunodominant regions recognized by cytolytic T lymphocytes in the Human Immunodeficiency Virus type 1 Nef protein", *Journal of Virology*, vol. 68, No. 11, Nov. 1994, pp. 736-7343.
By Barbary A. Torres et al., "Identification of an HIV-1 NEF Peptide that Binds to HLA Class II Antigens", *Biochemical and Biophysical Research Communications*, vol. 200, No. 2, Apr. 1994, pp. 1059-1065.
By I.P. Hunziker et al., "Who Is Right? Or, How to Judge the Disagreement about HLA Restriction of Nef Peptides", *AIDS Research and Human Retroviruses*, vol. 14, No. 11, Jul. 1998, pp. 921-924.
By. M. Muller et al., "Identification of seroreactive regions of the human papillomavirus type 16 proteins E4, E6, E7, and L1,", *Journal of General Virology, Society for General Microbiology, Reading*, vol. 71, Jan. 1990, pp. 2709-2717.
By Maya Shally et al., The E6 variant proteins E6I-E6IV of human papillomavirus 16: expression of cell free systems and bacteria and study of their interaction with p53, *Virus Research*, vol. 42, 1996, Amsterdam, Netherlands, pp. 81-96.

* cited by examiner

*Primary Examiner*—Ali R. Salimi
(74) *Attorney, Agent, or Firm*—Young & Thompson

(57)    ABSTRACT

Polyepitopic peptides of E6 and E7 proteins of Human Papillomavirus, their production, and methods of treating pathologies in which a polyepitopic peptide of the E6 and E7 protein of Human Papillomavirus is recognized by the cellular immune system.

2 Claims, 2 Drawing Sheets

FIGURE 1

E6 protein of HPV16

MHQKRTAMFQDPQERPRKLPQLCTELQTTIHDIILECVYCKQQLLRREVYDFA
FRDLCIVYRDGNPYAVCDKCLKFYSKISEYRHYCYSLYGTTLEQQYNKPLCDL
LIRCINCQKPLCPEEKQRHLDKKQRFHNIRGRWTGRCMSCCRSSRTRRETQL

FIGURE 2

E7 protein of HPV16

```
                              ——B7, B35——
                                   ——A29, B44——
           ——A2——                 ——A1——
   ——B35——      ——A1, B18——       ——B18——
       ——B44——   ——B62——
MAGDTPTLHEYMLDLQPETTDLYCYEQLNDSSEEEDEIDGPAGQAEPDRAHY
3                        25                       44

——A3, A11——              ——A2——
——B7, B35——       ——A29, B44——    ——A3, A11——
NIVTFCCKCDSTLRLCVQSTHVDIRTLEDLLMGTLGIVCPICSQKP
60              79                        97
```

POLYEPITOPIC PROTEIN FRAGMENTS OF THE E6 AND E7 PROTEINS OF HPV, THEIR PRODUCTION AND THEIR USE PARTICULARLY IN VACCINATION

CROSS REFERENCE TO RELATED APPLICATIONS

This application is a division of application Ser. No. 09/980,523, filed on Apr. 29, 2002, application Ser. No. 09/980,523, now U.S. Pat. No. 6,783,763, is the national phase of PCT International Application No. PCT/FR00/01513 filed on May 31, 2000 under 35 U.S.C. § 371, the entire contents of which are hereby incorporated by reference.

BACKGROUND OF THE INVENTION

The present invention has for its object polyepitopic protein fragments, such as those of the E6 and E7 proteins of human papillomavirus, or of the human p53 protein, their process of production, and their uses, particularly in the field of therapeutic or preventive vaccination.

SUMMARY OF THE INVENTION

The invention more particularly has for its object the use of polyepitopic fragments of a predetermined protein for the preparation of medications adapted for the prevention or treatment of pathologies in which said protein is recognized by the cellular immune system.

BRIEF DESCRIPTION OF THE DRAWINGS

FIG. 1 shows an E6 protein of HPV 16;
FIG. 2 shows an E7 protein of HPV 16.

DETAILED DESCRIPTION OF THE INVENTION

Preferably, said polyepitopic fragments are such that their N-terminal amino acid corresponds to the N-terminal amino acid of the epitope located upstream of one or several other epitopes of a polyepitopic region of said protein, and their C-terminal amino acid corresponds to the C-terminal amino acid of the epitope located downstream of the above-mentioned epitope or epitopes of said polyepitopic region.

Thus, the above-mentioned polyepitopic protein fragments of the present invention correspond preferably to the polyepitopic regions of a predetermined protein, namely to the regions containing several epitopes recognized by the T cells in association with the different molecules of the major complex of histocompatibility (MCH), said regions being selected from those having the characteristic of being degraded in vitro in shorter peptides by proteasomes, such as the 20S proteasome, when the protein fragment tested is placed in the presence of said proteasome, particularly according to the following detailed method. The protein fragment (about 75 µg when it is a polypeptide of about 30 amino acids) is incubated at 37° C. with about 15 µg of 20S proteasome (Calbiochem Ref 539150, La Jolla, Calif., USA) in 500 µl of the following buffer: 20 mM Tris-HCl pH8, 0.5 mM EDTA. Aliquots of 50 µl are removed after incubation times of 24 and 48 hours, and are analyzed by high pressure liquid chromatography (HPLC). The digestion products of the proteasomes are separated by RP-HPLC (Perkin Elmer) by using a C18 column and an acetonitrile gradient (from 0 to 100% containing 0.1% trifluoroacetic acid, for 90 minutes, elution rate 0.8 ml/min). The cleavage products are detected at 214 nm by an absorption detector (759A, Applied Biosystems).

Preferably, the polyepitopic regions defined above have the characteristic of containing hydrophobic amino acids.

The different epitopes of the polyepitopic region of the predetermined protein, and delimiting the epitopic protein fragments, are preferably selected from the peptides;
  binding to a predetermined molecule of MCH, particularly to a molecule of the predetermined HLA type, and this from concentrations of about $10^{-6}$ M to about $10^{-10}$ M in peptide for concentrations of about $10^{-7}$ M of HLA molecules, particularly under the conditions described hereafter,
  and forming a stable complex with said MCH molecule, namely particularly a complex in which said peptide remains bound to said molecule for at least about 3 hours at 37° C.

By way of illustration, the above-mentioned epitopes of the invention are selected from among the peptides adapted:
  on the one hand of associating with the molecules of MCH, particularly by using the following method:
    incubation (particularly for about 2 hours at 25° C., then about 15 hours at 4° C.) of the peptide in the presence of MCH molecules, from the lysis of human or animal cells, or purified particularly by affinity chromatography from human or animal cell lines,
    trapping complexes formed during the preceding step on a solid support covered with a first antibody, particularly monoclonal, recognizing specifically the CMH molecules in their configuration dependent on their connection to said peptide,
    addition to the preceding solid support of a second marked antibody, particularly by coupling to a radioactive, enzymatic or fluorescent marker, said marked antibody recognizing specifically either the long chains of MCH in their configuration dependent on their connection to the peptide, or the short chain of MCH or the β2-microglobulin binding specifically to the different long chains of the MCH in their above-mentioned configuration,
    detection, after rinsing of the solid support, of the possible presence of the second marked antibody remaining fixed on the solid support, signifying an association effect between the molecules of MCH and the peptide studied,
  and, on the other hand, forming a complex with said MCH molecules, whose stability can be evaluated by the use of a method of following according to time the connection established between the peptide and the MCH molecules, this method being preferably carried out according to a protocol identical to the preceding method, but in which the incubation step of the peptide in the presence of MCH molecules on the solid support covered with said first antibody, is preceded by a preliminary step of eliminating the free peptide adapted that may be present in the reaction medium, particularly by washing the solid support, said incubation step being carried out (preferably at a temperature of 37° C.) for variable times of 1 hours, 3 hours, 5 hours, 24 hours and 48 hours.

As mentioned above, the epitopes of the invention should be recognized by the T cells in association with the MCH molecules and associate with these latter, particularly in the framework of the practice of the recognition test described above. This association can be weak (detectable at concentrations of peptide analogs of the order of $10^{-4}$ to $10^{-5}$ M), intermediate (detectable at concentrations of peptide analogs of the order of $10^{-6}$ to $10^{-7}$ M), or strong (detectable at concentrations of peptide analogs of the order of $10^{-8}$ to $10^{-9}$ M). The peptides associated with the MCH molecules in the scope of the present invention are preferably adapted to bond during at least about 3 hours, to said MCH molecules.

The invention more particularly has for its object the epitopes (also designated peptides above and hereafter) as described above and characterized in that they are selected from among those adapted:
- to induce in vitro cytolysis by cytotoxic T lymphocytes, of target cells having at their surface the above-mentioned peptide associated with the MCH molecules, said cytotoxic T lymphocytes being preferably removed from a patient having a pathology in which the peptide studied is implied,
- and inducing in vitro the secretion of cytokines (or interleukines) by the above-mentioned cytotoxic T lymphocytes, particularly IL-2, IL-4 or γ interferon.

As the case may be, the above-mentioned epitopes are selected from those able to induce in vitro the appearance and the growth of cytotoxic T lymphocytes from animal or human cells, particularly from peripheral blood mononucleated cells (PBMC), in the presence of factors necessary for the growth and differentiation of the cytotoxic T cells.

The polyepitopic protein fragments of the invention are moreover characterized in that they are adapted to contain CD4 epitopes recognized by auxiliary T cells in association with the MCH molecules of class II, this property favoring the induction and maintenance of the CD8⁺ T cells recognizing the epitopes comprised in said fragments.

The present invention is illustrated with the help of FIGS. 1 (SEQ ID NO: 2) and 2 (SEQ ID NO: 12), showing respectively peptide sequences of the E6 (SEQ ID NO: 2) and E7 (SEQ ID NO: 12) proteins of the strain 16 of the human papillomavirus (HPV 16), as well as the polyepitopic fragments of the invention, and the epitopes within these fragments.

The invention more particularly has for its object the polyepitopic fragments of the E6 and E7 protein of HPV, and more particularly those of the E6 protein shown in FIG. 1, or by SEQ ID NO: 2, or those of the E7 protein, shown in FIG. 2, or by SEQ ID NO: 11, of HPV 16, characterized in that they comprise a peptide sequence of about 15 to about 30 amino acids, this peptide sequence containing the amino acid sequences of at least 3 different epitopes, and preferably at least 4 different epitopes binding stably to HLA molecules of identical or different type, when these epitopes are obtained by enzymatic degradation of said peptide sequence, particularly in the proteasome, such that at least 4 HLA molecules of different types, and preferably at least 5 HLA molecules of different types, bind to these epitopes, these 4 or 5 HLA molecules being selected from those of type A1, A2, A3, A11, A24, A29, B7, B8, B18, B27, B35, B44, B51, and B62.

Preferably, the polyepitopic fragments according to the invention are such that the number of amino acids of their peptide sequence is greater than or equal to 17, and less than or equal to 30.

The invention relates more particularly to the polyepitopic fragments of the E6 protein of HPV defined above, characterized in that they comprise a peptide sequence of about 15 to 30 amino acids, this peptide sequence containing amino acid sequences of at least 5 different epitopes, and preferably at least 6 different epitopes binding stably to HLA molecules of identical or different type, when these epitopes are obtained by enzymatic degradation of said peptide sequence, particularly in the proteasome, such that at least 6 HLA molecules of different types, and preferably at least 7 HLA molecules of different types, bind to these epitopes, these 6 or 7 HLA molecules being selected from those of type A1, A2, A3, A11, A24, A29, B7, B8, B18, B27, B35, B44, and B51.

Preferably, the polyepitopic fragments of the E6 protein according to the invention are such that the number of amino acids of their peptide sequence is greater than or equal to 20 (preferably greater than or equal to 22), and less than or equal to 30.

Also preferably, the above-mentioned polyepitopic fragments of the E6 protein of HPV, are characterized in that they all comprise an epitope binding to the HLA molecule of type B35, an epitope binding to the HLA molecule of type B44, and an epitope binding to the HLA molecule of type B51.

The invention more particularly has for its object the polyepitopic fragment of the E6 protein of HPV as defined above, characterized in that it corresponds to the fragment of 30 amino acids delimited by the amino acids located in positions 15 and 44 of the peptide sequence of the E6 protein of HPV, and characterized by the peptide sequence SEQ ID NO: 4 as follows:

(15)RPRKLPQLCTELQTTIHDIILECVYCKQQL(44)

said fragment containing 9 epitopes binding stably to at least one of the 8 HLA molecules of the following types: A2, A11, A29, B7, B8, B35, B44, or B51, said epitopes being the following:
- (15)RPRKLPQL(22) (residues 15 to 22 of SEQ ID NO: 2) binding stably to HLA molecules of the B7 or B35 type,
- (18)KLPQLCTEL(26) (residues 18 to 26 of SEQ ID NO: 2) binding stably to HLA molecules of the A2 type,
- (19)LPQLCTEL(26) (residues 19 to 26 of SEQ ID NO: 2) binding stably to HLA molecules of the B51 type,
- (21)QLCTELQTTI(30) (residues 21 to 30 of SEQ ID NO: 2) binding stably to HLA molecules of the A2 type,
- (24)TELQTTIHDI(33) (residues 24 to 33 of SEQ ID NO: 2) binding stably to HLA molecules of the A29 or B44 type,
- (29)TIHDIILRCV(38) (residues 29 to 38 of SEQ ID NO: 2) binding stably to HLA molecules of the A2 type,
- (33)IILECVYCK(41) (residues 33 to 41 of SEQ ID NO: 2) binding stably to HLA molecules of the A11 type,
- (35)LECVYCKQQL(44) (residues 35 to 44 of SEQ ID NO: 2) binding stably to HLA molecules of the A29 or B44 type,
- (37)CVYCKQQL(44) (residues 37 to 44 of SEQ ID NO: 2) binding stably to HLA molecules of the B8 type.

The invention also relates to the polyepitopic fragment of the E6 protein of HPV as defined above, characterized in that it corresponds to the fragment of 17 amino acids delimited by the amino acids located at positions 46 and 62, or to the fragment of 22 amino acids delimited by the amino acids located at positions 46 and 67 of the peptide sequence of the E6 protein of HPV, this latter fragment being characterized by the peptide sequence SEQ ID NO: 6 as follows:

(46)RREVYDFAFRDLCIVYRDGNPY(67)

said fragment containing 6 epitopes binding stably to at least one of the 10 HLA molecules of the following types: A2, A3, A11, A24, A29, B7, B27, B35, B44, or B51, said epitopes being the following:

(46)RREVYDFAFR(55) (residues 46 to 55 of SEQ ID NO: 2) binding stably to HLA molecules of the B27 type,
(49)VYDFAFRDL(57) (residues 49 to 57 of SEQ ID NO: 2) binding stably to HLA molecules of the A24 type,
(50)YDFAFRDL(57) (residues 50 to 57 of SEQ ID NO: 2) binding stably to HLA molecules of the A29 or B44 type,
(52)FAFRDLCIV(60) (residues 52 to 60 of SEQ ID NO: 2) binding stably to HLA molecules of the A2, B35, B51, or B7 type,
(54)FRDLCIVYR(62) (residues 54 to 62 of SEQ ID NO: 2) binding stably to HLA molecules of the A3 or A11 type,
(59)IVYRDGNPY(67) (residues 59 to 67 of SEQ ID NO: 2) binding stably to HLA molecules of the A3 or A11 type.

The invention also has for its object the polyepitopic fragment of the E6 protein of HPV as defined above, characterized in that it corresponds to the fragment of 29 amino acids delimited by the amino acids located at positions 80 and 108 of the peptide sequence of the E6 protein of HPV, this latter fragment being characterized by the peptide sequence SEQ ID NO: 8 as follows:

(80)ISEYRHYCYSLYGTTLEQQYNKPLCDLLI(108)

said fragment containing 6 epitopes binding stably to at least 10 HLA molecules of the following types: A1, A3, A11, A24, A29, B7, B18, B35, B44, or B51, said epitopes being the following:
 (80)ISEYRHYCY(88) (residues 80 to 88 of SEQ ID NO: 2) binding stably to HLA molecules of the A1 or B18 type,
 (81)SEYRHYCY(88) (residues 81 to 88 of SEQ ID NO: 2) binding stably to HLA molecules of the A29 or B44 type,
 (87)CYSLYGTTL(95) (residues 87 to 95 of SEQ ID NO: 2) binding stably to HLA molecules of the A24 type,
 (94)TLEQQYNK(101) (residues 94 to 101 of SEQ ID NO: 2) binding stably to HLA molecules of the A3 or A11 type,
 (95)LEQQYNKPL(103) (residues 95 to 103 of SEQ ID NO: 2) binding stably to HLA molecules of the A29 or B44 type,
 (101)KPLCDLLI(108) (residues 101 to 108 of SEQ ID NO: 2) binding stably to HLA molecules of the B7, B35 or B51 type.

The invention more particularly has for its object the polyepitopic fragment of the E6 protein of HPV as defined above, characterized in that it corresponds to the fragment of 22 amino acids delimited by the amino acids located at positions 118 and 139 of the peptide sequence of the E6 protein of HPV, this latter fragment being characterized by the peptide sequence SEQ ID NO: 10 as follows:

(118)CPEEKQRHLDKKQRFHNIRGRW(139)

said fragment containing 6 epitopes binding stably to at least one of the 7 HLA molecules of the following types: A24, B8, B18, B27, B35, B44, or B51, said epitopes being the following:
 (118)CPEEKQRHL(126) (residues 118 to 126 of SEQ ID NO: 2) binding stably to HLA molecules of the B8, B18, B35, B51 type,
 (119)PEEKQRHL(126) (residues 119 to 126 of SEQ ID NO: 2) binding stably to HLA molecules of the B44 type,
 (127)DKKQRFHNI(135) (residues 127 to 135 of SEQ ID NO: 2) binding stably to HLA molecules of the B8 type,
 (128)KKQRFHNIR(136) (residues 128 to 136 of SEQ ID NO: 2) binding stably to HLA molecules of the B27 type,
 (130)QRFHNIRGRW(139) (residues 130 to 139 of SEQ ID NO: 2) binding stably to HLA molecules of the B27 type,
 (131)RFHNIRGRW(139) (residues 131 to 139 of SEQ ID NO: 2) binding stably to HLA molecules of the A24 type.

The invention also relates to the polyepitopic fragments of the E7 protein of HPV as defined above, characterized in that they comprise a peptide sequence of about 15 to 30 amino acids, this peptide sequence containing the amino acid sequences of at least 3 different epitopes, and preferably of at least 4 different epitopes binding stably to HLA molecules of the identical or different type, when these epitopes are obtained by enzymatic degradation of said peptide sequence, particularly in the proteasome, such that at least 4 HLA molecules of different types, and preferably at least 5 HLA molecules of different types bind to these epitopes, these 4 or 5 HLA molecules being selected from those of type A1, A2, A3, A11, A29, B7, B18, B35, B44, and B62.

Preferably, the polyepitopic fragments of the E7 protein according to the invention are such that the number of amino acids of the peptide sequence is greater than or equal to 17, and less than or equal to 23.

Again preferably, the polyepitopic fragments of the E7 protein of the above-mentioned HPV, are characterized in that they all comprise an epitope binding to the HLA molecule of type B44.

The invention more particularly has for its object the polyepitopic fragment of the E7 protein of HPV as defined above, characterized in that it corresponds to the fragment of 23 amino acids delimited by the amino acids located in positions 3 and 25 of the peptide sequence of the E7 protein of HPV, this latter fragment being characterized by the peptide sequence SEQ ID NO: 14 as follows:
 (3)GDTPTLHEYMLDLQPETTDLYCY(25)
said fragment containing 5 epitopes binding stably to at least one of the 6 HLA molecules of the following type: A1, A2, B18, B35, B44 or B62, said epitopes being the following:
 (3)GDTPTLHEY(11) (residues 3 to 11 of SEQ ID NO: 12) binding stably to HLA molecules of the B44 type,
 (5)TPTLHEYML(13) (residues 5 to 13 of SEQ ID NO: 12) binding stably to HLA molecules of the B35 type,
 (11)YMLDLQPETT(20) (residues 11 to 20 of SEQ ID NO: 12) binding stably to HLA molecules of the A2 type,
 (15)LQPETTDLY(23) (residues 15 to 23 of SEQ ID NO: 12) binding stably to HLA molecules of the B62 type,
 (16)QPETTDLYCY(25) (residues 16 to 25 of SEQ ID NO: 12) binding stably to HLA molecules of the A1 or B18 type.

The invention also relates to the polyepitopic fragment of the E7 protein of HPV as defined above, characterized in that it corresponds to the fragment of 17 amino acids delimited by the amino acids located in positions 44 and 60 of the peptide sequence of the E7 protein of HPV, this latter fragment being characterized by the peptide sequence SEQ ID NO: 16 as follows:

(44)QAEPDRAHYNIVTFCCK(60)

said fragment containing 4 epitopes binding stably to at least one of the 6 HLA molecules of the following types: A1, A3, A11, A29, B7, B18, B35, or B44, said epitopes being the following:
 (44)QAEPDRAHY(52) (residues 44 to 52 of SEQ ID NO: 12) binding stably to HLA molecules of the A1 or B18 type, (45)AEPDRAHY(52) (residues 45 to 52 of SEQ ID NO: 12) binding stably to HLA molecules of the A29 or B44 type, (46)EPDRAHYNIV(55) (residues 46 to 55 of SEQ ID NO: 12) binding stably to HLA molecules of the B7 or B35 type, (53)NIVTFCCK(60) (residues 53 to 60 of SEQ ID NO: 12) binding stably to HLA molecules of the A3 or A11 type.

The invention also has for its object the polyepitopic fragment of the E7 protein of HPV as defined above, characterized in that it corresponds to the fragment of 19 amino acids delimited by the amino acids located in positions 79 and 97 of the peptide sequence of the E7 protein of HPV, this latter fragment being characterized by the peptide sequence SEQ ID NO: 18 as follows:

(79)LEDLLMGTLGIVCPICSQK(97)

said fragment containing 4 epitopes binding stably to at least one of the 5 HLA molecules of the following types: A2, A3, A11, A29 or B44, said epitopes being the following:

(79)LEDLLMGTL(87) (residues 79 to 87 of SEQ ID NO: 12) binding stably to HLA molecules of the A29 or B44 type, (82)LLMGTLGIV(90) (residues 82 to 90 of SEQ ID NO: 12) binding stably to HLA molecules of the A2 type, (86)TLGIVCPI(93) (residues 86 to 93 of SEQ ID NO: 12) binding stably to HLA molecules of the A2 type, (89)IVCPICSQK(97) (residues 89 to 97 of SEQ ID NO: 12) binding stably to HLA molecules of the A3 or A11 type.

The invention also has for its object the polyepitopic fragments of the p53 human protein characterized in that they comprise a peptide sequence of about 20 to about 35 amino acids, this latter containing amino acid sequences of at least three different epitopes binding stably to HLA molecules of identical or different type, when these epitopes are obtained by enzymatic degradation of said peptide sequence, particularly in the proteasome, such that at least 3 HLA molecules of different types will be recognized by said epitopes and will bind to these latter, these 3 HLA molecules being selected from those of type A1, A2, A3, A24, B7, B8, B27, B35, B44 and B62.

The invention also relates to the polyepitopic fragments of the p53 human protein mentioned above, characterized in that they comprise a peptide sequence of about 20 to about 35 amino acids, this latter containing the amino acid sequences of at least 5 different epitopes, and preferably of at least 6 different epitopes binding to HLA molecules of identical or different type, such that at least 3 HLA molecules of different types, and preferably at least 4 HLA molecules of different types will be recognized by said epitopes and will bind to these latter, these 3 or 4 HLA molecules being selected from those of type A2, A24, B27, B35, B44 and B62.

The invention more particularly has for its object the polyepitopic fragment of the p53 human protein as defined above, characterized in that it corresponds to the fragment of 32 amino acids delimited by the amino acids located in positions 106 and 137 of the peptide sequence of the p53 protein, or to the fragment of 36 amino acids delimited by the amino acids in positions 102 and 137 of said peptide sequence, this latter fragment being characterized by the following peptide sequence:

(SEQ ID NO: 19)
(102)TYQGSYGFRLGFLHSGTAKSVTCTYSPALNKMFCQL(137)

said fragment containing 6 epitopes binding stably to at least one of the 4 HLA molecules of the following types: A2, A24, B35 or B62, said epitopes being the following:

(102)TYQGSYGFRL(111) (residues 1 to 10 of SEQ ID NO: 19) binding stably to HLA molecules of the A24 type, (105)GSYGFRLGFL(114) (residues 4 to 13 of SEQ ID NO: 19) binding stably to HLA molecules of the B35 type, (106)SYGFRLGFL(114) (residues 5 to 13 of SEQ ID NO: 19) binding stably to HLA molecules of the A24 type, (118)TAKSVTCTY(126) (residues 17 to 25 of SEQ ID NO: 19) binding stably to HLA molecules of the B62 type, (125)TYSPALNKMF(134) (residues 24 to 33 of SEQ ID NO: 19) binding stably to HLA molecules of the A24 type, (129)ALNKMFCQL(137) (residues 28 to 36 of SEQ ID NO: 19) binding stably to HLA molecules of the B35 type.

The invention also has for its object the polyepitopic fragment of the p53 human protein as defined above, characterized in that it corresponds to the fragment of 21 amino acids delimited by the amino acids located in the positions 149 and 169 of the peptide sequence of the p53 protein, and characterized by the following peptide sequence:

(149)STPPPGTRVRAMIYKQSQHM(169)    (SEQ ID NO: 20)

said fragment containing 6 epitopes binding stably to at least one of the 6 HLA molecules of the following types: A2, A3, A24, B27, B35 or B62, said epitopes being the following:

(149)STPPPGTRV(157) (residues 1 to 9 of SEQ ID NO: 20) binding stably to HLA molecules of the A2 type, (152)PPGTRVRAM(160) (residues 4 to 12 of SEQ ID NO: 20) binding stably to HLA molecules of the B35 type, (155)TRVRAMAIYK(164) (residues 7 to 16 of SEQ ID NO: 20) binding stably to HLA molecules of the B27 type, (156)RVRAMAIY(163) (residues 8 to 15 of SEQ ID NO: 20) binding stably to HLA molecules of the B62 type, (156)RVRAMAIYK(164) (residues 8 to 16 of SEQ ID NO: 20) binding stably to HLA molecules of the A3 type, (162)IYKQSQHM(169) (residues 14 to 21 of SEQ ID NO: 20) binding stably to HLA molecules of the A24 type.

The invention also relates to the polyepitopic fragment of the p53 human protein as defined above, characterized in that it corresponds to the fragment of 26 amino acids delimited by the amino acids located in positions 187 and 212 of the peptide sequence of the p53 protein, or to the fragment of 34 amino acids delimited by the amino acids located in positions 187 and 220 of said peptide sequence, this latter fragment being characterized by the following peptide sequence:

(SEQ ID NO: 21)
(187)GLAPPQHLIRVEGNLRVEYLDDRNTFRHSVVVPY(220)

said fragment containing 11 epitopes binding stably to at least one of the 7 HLA molecules of the following types: A1, A2, A24, B7, B8, B27 or B44, said epitopes being the following:
- (187)GLAPPQHLIRV(197) (residues 1 to 11 of SEQ ID NO: 21) binding stably to HLA molecules of the A2 type,
- (189)APPQHLIRV(197) (residues 3 to 11 of SEQ ID NO: 21) binding stably to HLA molecules of the B7 type,
- (195)IRVEGNLRVEY(205) (residues 9 to 19 of SEQ ID NO: 21) binding stably to HLA molecules of the B27 type,
- (196)RVEGNLRVEY(205) (residues 10 to 19 of SEQ ID NO: 21) binding stably to HLA molecules of the A2 type,
- (197)VEGNLRVEY(205) (residues 11 to 19 of SEQ ID NO: 21) binding stably to HLA molecules of the B44 type,
- (201)LRVEYLDDR(209) (residues 15 to 23 of SEQ ID NO: 21) binding stably to HLA molecules of the B27 type,
- (203)VEYLDDRNTF(212) (residues 17 to 26 of SEQ ID NO: 21) binding stably to HLA molecules of the B44 type,
- (204)EYLDDRNTF(212) (residues 18 to 26 of SEQ ID NO: 21) binding stably to HLA molecules of the A24 type,
- (210)NTFRHSVVV(218) (residues 24 to 32 of SEQ ID NO: 21) binding stably to HLA molecules of the B8 type,
- (211)TFRHSVVV(218) (residues 25 to 32 of SEQ ID NO: 21) binding stably to HLA molecules of the A24 type,
- (212)FRHSVVVPY(220) (residues 26 to 34 of SEQ ID NO: 21) binding stably to HLA molecules of the B27 type.

The invention also has for its object the polyepitopic fragment of the p53 human protein as defined above, characterized in that it corresponds to the fragment of 18 amino acids delimited by the amino acids located in positions 226 and 243 of the peptide sequence of the p53 protein, and characterized by the following peptide sequence:

(226)GSDCTTIHYNYMCNSSCM(243)    (SEQ ID NO: 22)

said fragment containing 3 epitopes binding stably to at least one of the 3 HLA molecules of the following types: A1, A24 or B44, said epitopes being the following:
- (226)GSDCTTIHY(234) (residues 1 to 9 of SEQ ID NO: 22) binding stably to HLA molecules of the A1 type,
- (227)SDCTTIHYNY(236) (residues 2 to 11 of SEQ ID NO: 22) binding stably to HLA molecules of the B44 type,
- (235)NYMCNSSCM(243) (residues 10 to 18 of SEQ ID NO: 22) binding stably to HLA molecules of the A24 type.

The invention also relates to the polyepitopic fragment of the p53 human protein as defined above, characterized in that it corresponds to the fragment of 25 amino acids delimited by the amino acids located in positions 249 and 273 of the peptide sequence of the p53 protein, or to the fragment of 26 amino acids delimited by the amino acids located in positions 248 and 273 of said peptide sequence, or to the fragment of 33 amino acids delimited by the amino acids located in positions 248 and 280 of said peptide sequence, this latter fragment being characterized by the following peptide sequence:

(SEQ ID NO: 23)
(248)RRPILTIITLEDSSGNLLGRNSFEVRVCACPGR(280)

said fragment containing 8 epitopes binding stably to at least one of the 6 HLA molecules of the following types: A2, B7, B27, B35, B44 or B62, said epitopes being the following:
- (248)RRPILTIITL(257) (residues 1 to 10 of SEQ ID NO: 23) binding stably to HLA molecules of the B27 type,
- (249)RPILTIITL(257) (residues 2 to 10 of SEQ ID NO: 23) binding stably to HLA molecules of the B35 and B7 type,
- (255)ITLEDSSGN(263) (residues 8 to 16 of SEQ ID NO: 23) binding stably to HLA molecules of the A2 type,
- (257)LEDSSGNLL(265) (residues 10 to 18 of SEQ ID NO: 23) binding stably to HLA molecules of the B44 type,
- (263)NLLGRNSF(270) (residues 16 to 23 of SEQ ID NO: 23) binding stably to HLA molecules of the B62 type,
- (264)LLGRNSFEV(272) (residues 17 to 25 of SEQ ID NO: 23) binding stably to HLA molecules of the A2 type,
- (266)GRNSFEVR(273) (residues 19 to 26 of SEQ ID NO: 23) binding stably to HLA molecules of the B27 type,
- (272)VRVCACPGR(280) (residues 25 to 33 of SEQ ID NO: 23) binding stably to HLA molecules of the B27 type.

The invention also relates to peptide sequences derived from the polyepitopic fragments mentioned above, of the E6 or E7 proteins, or of the p53 protein, particularly:
- by substitution and/or suppression and/or addition of one or several amino acids, of the above-mentioned fragments, and/or
- by modification of at least one peptide linkage —CO—NH— of the peptide chain of the above-mentioned fragments, particularly by introduction of a retro or retro-inverso type linkage, and/or
- by substitution of at least one amino acid of the peptide chain of the sequence or of the above-mentioned fragment, with a non-proteinogenic amino acid, said derived sequences containing peptides or pseudopeptides binding specifically to the same molecule or molecules of MCH as those binding to the peptides contained in the polyepitopic fragments mentioned above from which they derive.

By derived sequence by introduction of a retro-inverso linkage, should be understood any peptide analog of an above-mentioned fragment, said analog being constituted by a peptide chain in which at least one of the residues on the one hand is bound to at least one adjacent residue by an —NH—CO— linkage, and on the other hand, is of a chirality opposite that of the same amino acyl residue in the peptide chain of the parent peptide (namely of the above-mentioned fragment from which it derives).

By a sequence derived by introduction of a retro linkage, should be understood any peptide analog of an above-mentioned fragment, said analog being constituted by a peptide chain in which at least one of the residues is bound to at least one adjacent residue by an —NH—CO— linkage, the chirality of the whole of the amino acyl residues involved in at least one —NH—CO— linkage being conserved relative to the corresponding residues of the peptide chain of the parent peptide.

It follows that the —CO—NH— and —NH—CO— linkages must be taken into account in the preceding, in the direction of the parent peptide chain going from the amino terminal (N-terminal) end toward the carboxy terminal (C-terminal) end.

By "proteinogenic amino acid", is meant, in the preceding, any amino acid entering into the constitution of a natural protein or peptide.

By "non-proteinogenic amino acid" is meant, in contrast to the preceding definition, any amino acid that does not enter into the constitution of a natural protein or peptide. There is meant more particularly by "non-proteinogenic amino acid", any amino acid whose carbon carrying a R side chain, namely the —CHR— group, located between —CO— and —NH— in the natural peptide chain, is replaced by a structure that does not enter into the constitution of a natural protein or peptide.

The invention more particularly has for its object the derived sequences as described above, characterized in that at least one of the peptide linkages —CO—NH— of the peptide chain of the parent peptide is replaced by a linkage different from the —CO—NH— linkage, said different linkage being particularly selected from the following.

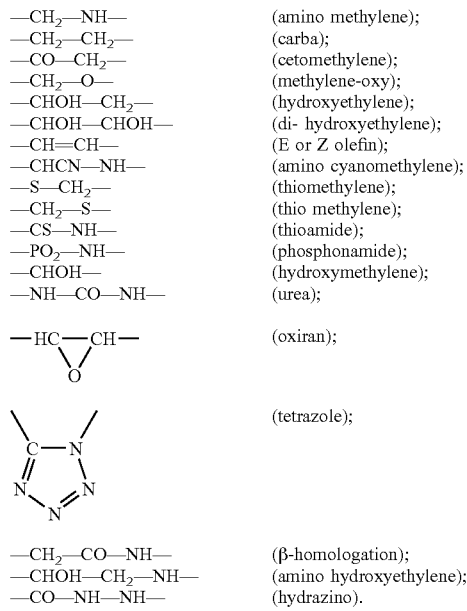

| | |
|---|---|
| —CH₂—NH— | (amino methylene); |
| —CH₂—CH₂— | (carba); |
| —CO—CH₂— | (cetomethylene); |
| —CH₂—O— | (methylene-oxy); |
| —CHOH—CH₂— | (hydroxyethylene); |
| —CHOH—CHOH— | (di- hydroxyethylene); |
| —CH=CH— | (E or Z olefin); |
| —CHCN—NH— | (amino cyanomethylene); |
| —S—CH₂— | (thiomethylene); |
| —CH₂—S— | (thio methylene); |
| —CS—NH— | (thioamide); |
| —PO₂—NH— | (phosphonamide); |
| —CHOH— | (hydroxymethylene); |
| —NH—CO—NH— | (urea); |
| —HC—CH— (with O bridge) | (oxiran); |
| tetrazole ring | (tetrazole); |
| —CH₂—CO—NH— | (β-homologation); |
| —CHOH—CH₂—NH— | (amino hydroxyethylene); |
| —CO—NH—NH— | (hydrazino). |

The invention also has for its object nucleotide sequences coding for a polyepitopic fragment of the E6 or E7 protein, or for a derived peptide sequence, as defined above, said nucleotide sequences being derived from the sequence SEQ ID NO: 1 coding for the E6 protein, or from the sequence SEQ ID NO: 11 coding for the E7 protein.

In this connection, the invention more particularly has for its object the nucleotide sequences defined above, selected from the following:
the sequence SEQ ID NO: 3, coding for the polyepitopic fragment SEQ ID NO: 4 mentioned above, of the E6 protein,
the sequence SEQ ID NO: 5, coding for the polyepitopic fragment SEQ ID NO: 6 mentioned above, of the E6 protein,
the sequence SEQ ID NO: 7, coding for the polyepitopic fragment SEQ ID NO: 8 mentioned above, of the E6 protein,
the sequence SEQ ID NO: 9, coding for the polyepitopic fragment SEQ ID NO: 10 mentioned above, of the E6 protein,
the sequence SEQ ID NO: 13, coding for the polyepitopic fragment SEQ ID NO: 14 mentioned above, of the E7 protein,
the sequence SEQ ID NO: 15, coding for the polyepitopic fragment SEQ ID NO: 16 mentioned above, of the E7 protein,
the sequence SEQ ID NO: 17, coding for the polyepitopic fragment SEQ ID NO: 18 mentioned above, of the E7 protein.

The invention also has for its object the nucleotide sequences coding for a polyepitopic fragment of the p53 protein, or for a derived peptide sequence, as defined above.

The invention also has for its object any vector, particularly a plasmid, cosmid or phage, containing at least one above-mentioned nucleotide sequence under the control of elements necessary for the transcription of said sequence, particularly under the control of a transcription promoter and terminator.

The invention also relates to host cells, particularly bacterial, virus, yeasts, eucaryotic cells, transformed with the help of a vector mentioned above according to the invention, so as to integrate stably into their genome or to maintain in a stable manner in their cytoplasm, at least one nucleotide sequence according to the invention.

The invention also relates to any vector comprising one or several polyepitopic fragments and/or one or several derived peptide sequences as defined above, or any vector comprising one or several above-mentioned nucleotide sequences, said vectors being selected from those adapted to ensure protection of said fragments or nucleotide sequences in the organism and/or their penetration into the cells of the organism.

In the case of the use of polyepitopic fragments and/or the above-mentioned derived peptide sequences, such vectors are selected from fatty acids (in the framework of the preparation of lipopeptides), liposomes, etc.

In this connection, the invention more particularly has for its object any lipopeptide characterized in that it comprises:
a peptide portion comprising one or several polyepitopic protein fragments selected from those defined above, or any peptide sequence derived from said fragments as defined above,
and one or several lipophilic portions, preferably selected from those comprising:
a C4 to C20 hydrocarbon chain, saturated or unsaturated, linear or branched,
or a steroid group, as the case may be connected to the above-mentioned hydrocarbon chain,
said lipophilic portions being if desired associated with a short peptide vector (thereby to form lipopeptide vector structures) comprising one or several ionized functions at physiological pH, and a function permitting the covalent bonding of said hydrocarbon chain and/or said steroid group.

By lipophilic portion, in what precedes and what follows, is intended any lipophilic molecule, insoluble in water, permitting, when it is linked to the peptide portion defined above, an intracellular passive passage of the obtained lipopeptide, thanks to the hydrophobic properties of said molecule. Preferably the lipopeptide resulting from the linking of the lipophile portion to the peptide portion, is soluble in water.

Preferably, the hydrocarbon chain of the lipophilic portions, is selected from the following:
 palmitic acid,
 oleic acid,
 linoleic acid,
 linolenic acid.

Also preferably, the steroid group of the lipophilic portion or portions is selected from cholesterol derivatives such as cholest-5-enyl-3-oxy acetic acid, or cholest-5-enyl-3-oxy-carbonic acid.

The invention more particularly has for its object any lipopeptide as described above, characterized in that the lipophilic portion or portions are bonded covalently to one or several amino acids of the peptide portion.

Preferably, the lyophilic portion or portions are bonded covalently to the $\alpha NH_2$ or $\epsilon NH_2$ function of a lysine located in the N terminal or C terminal position of the peptide portion, or to the thiol function of a cystein, or to any amino, alcohol or thiol function if desired added to this peptide with a single spacer.

In this connection, the invention more particularly has for its object any lipopeptide as defined above, in which the lipophilic portion or portions are represented by a group $N^\alpha$-acetyl-Lysine $N^\epsilon$(palmitoyl) (also designated by the abbreviation Ac—K(Pam)).

The present invention also has for its object micelles or microaggregates of one or several different lipopeptides defined above.

Preferably, said micelles or microaggregates have a size less than about 1 μm.

Preferably, the micelles or microaggregates according to the invention are as obtained by dispersion of said lipopeptides in a concentrated acetic acid solution of about 80%, or any other solvent capable of ensuring molecular dispersion of the lipopeptides in solution.

In the case of the use of nucleotide sequences defined above according to the invention, the above-mentioned vectors are selected from the viruses, particularly the retroviruses, the adenoviruses and the associated viruses (AAV Adeno Associated Virus).

The invention also has for its object antibodies directed against the polyepitopic protein fragments or the epitopes or their derived peptide sequences (or analogs) as defined above, said antibodies being those obtained by immunization of an animal with at least one of the above-mentioned complexes, said antibodies being adapted to form a complex with these polyepitopic fragments or these epitopes or their analogs.

The antibodies according to the invention are polyclonal or monoclonal antibodies.

The polyclonal antibodies mentioned above are obtained by immunization of an animal with at least one polyepitopic protein fragment or an epitope or an analog according to the invention, followed by the recovery of the desired antibodies in purified form, by removal of the serum of said animal, and separation of said antibodies from the other constituents of the serum, particularly by affinity chromatography on a column on which is fixed a specific antigen recognized by the antibody, particularly a polyepitopic protein fragment or an epitope or an analog according to the invention.

The monoclonal antibodies according to the invention can be obtained by the hybridome technique whose general principle is set forth below.

In a first instance, an animal is immunized, generally a mouse (or culture cells in an in vitro immunization framework) with a polyepitopic protein fragment or an epitope or an analog according to the invention, against which the B lymphocytes of the animal are then capable of producing antibodies. These antibody-producing lymphocytes are then fused with "immortal" myelomatous cells (particularly of mice) to give rise to hybridomes. From the heterogeneous mixture of cells thus obtained, there is then carried out a selection of the cells capable of producing a particular antibody and of multiplying indefinitely. This hybridome is multiplied in the form of clones, each leading to the production of a monoclonal antibody whose recognition properties relative to the polyepitopic protein fragment or epitope or the like of the invention, can be tested for example with ELISA, by immunotransfer in one or two dimensions, by immunofluorescence, or with the help of a biodetector. The monoclonal antibodies thus selected are then purified particularly according to the affinity chromatography technique described above.

The invention also relates to the use of one or several above-mentioned antibodies for practicing a diagnostic method in vitro of the above-mentioned pathologies.

In this connection, the invention also has for its object sets or kits comprising said antibodies, for practicing a diagnostic method as defined above.

The invention also relates to pharmaceutical compositions, or vaccines, characterized in that they comprise:
 a)
  at least one polyepitopic fragment of the E6 or E7 protein as defined above,
  and/or at least one peptide sequence derived from this fragment, as defined above,
  and/or at least one suitable vector, particularly lipopeptides and/or micelles defined above, containing at least one polyepitopic fragment mentioned above of the E6 or E7 protein, and/or at least one sequence mentioned above derived from these fragments,
 in association with a physiologically acceptable vehicle,
 said polyepitopic protein fragment and/or its derived sequence being, as the case may be, associated with one or several other exogenous epitopes recognized by auxiliary T cells (also called CD4 or T helper epitopes), said epitopes being selected particularly from the following:
 the peptide fragment delimited by amino acids located in positions 830 and 846 of the peptide sequence of the tetanus toxin, said fragment responding to the following formula: QYIKANSKFIGITELKK(SEQ ID NO: 24),
 hemagglutinin (Prevost-Blondel et al., 1995, J. Virol, 62, No. 12, pp 8046-8055),
 PADRE epitope (Alexander et al., 1994, Immunity, 1, 751).
 or b)
  at least one nucleotide sequence as defined above, coding for an above-mentioned polyepitopic fragment of the E6 or E7 protein,
  and/or at least one nucleotide sequence coding for a peptide sequence derived from this fragment, as defined above,
 the above-mentioned nucleotide sequences being adapted to be used alone, as minigenes,
  and/or at least one above-mentioned suitable vector, selected particularly from the viruses such as defined above, containing at least one above-mentioned nucleotide sequence, in association with a physiologically acceptable vehicle, or c)

antibodies defined above, directed against a polyepitopic fragment of the E6 or E7 protein, and/or against a peptide sequence derived from these fragments, as defined above, in association with a physiologically acceptable vehicle.

Preferably, the pharmaceutical compositions or vaccines mentioned above are present in a form administrable subcutaneously, particularly in several injections (preferably 3 injections) of about 500 µg of the polyepitopic fragment in the lipopeptide form, at about one month intervals.

The invention has more particularly for its object the use of polyepitopic fragments of the E6 or E7 protein defined above, or of the above-mentioned derived peptide sequences, or the above-defined nucleotide sequences, or the above-mentioned antibodies, or the lipopeptides defined above, for the preparation of a medication or vaccine for the prevention or treatment of pathologies connected with the infection of individuals by human papillomavirus, such as cervical intraepithelial neoplasias (CIN), the invasive cancer of the neck of the uterus, vulvar intraepithelial neoplasias (VIN).

The invention also relates to pharmaceutical compositions or vaccines characterized in that they comprise:

a)
at least one polyepitopic fragment of the p53 protein as defined above,
and/or at least one peptide sequence derived from this fragment, as defined above,
and/or at least one suitable vector, particularly the lipopeptides and/or micelles defined above, containing at least one above-mentioned polyepitopic fragment of the p53 protein, and/or at least one above-mentioned sequence derived from these fragments, in association with a physiologically acceptable vehicle, said polyepitopic protein fragment and/or its derived sequence being, as the case may be, associated with one or several other exogenous epitopes recognized by the auxiliary T cells (also called CD4 or T helper epitopes), said epitopes being selected particularly from those defined above, or b)
at least one nucleotide sequence as defined above, coding for an above-mentioned polyepitopic fragment of the p53 protein,
and/or at least one nucleotide sequence coding for a peptide sequence derived from this fragment, as defined above,
the above-mentioned nucleotide sequences being adapted to be used alone, as minigenes,
and/or at least one above-mentioned suitable vector, selected particularly from the viruses as defined above, containing at least one above-mentioned nucleotide sequence,
in association with a physiologically acceptable vehicle, or c)
antibodies defined above, directed against a polyepitopic fragment of the p53 protein, and/or against a peptide sequence derived from these fragments, as defined above, in association with a physiologically acceptable vehicle.

The invention also has for its object the use:
of at least one polyepitopic fragment of the p53 protein, selected from those defined above,
and/or at least one peptide sequence derived from this fragment, as defined above,
or at least one nucleotide sequence, as defined above, coding for a polyepitopic fragment of the p53 protein, and/or for a peptide sequence derived from this fragment, as defined above,
for the preparation of a medication or vaccine adapted for the prevention or treatment of cancers, particularly of the breast, of the colon, of the lung or of the bladder.

The invention also relates to peptides or epitopes of the E6 protein of HPV selected from the following:

(19)LPQLCTEL(26) (residues 19 to 26 of SEQ ID NO: 2) binding stably to HLA molecules of the B51 type,
(21)QLCTELQTTI(30) (residues 21 to 30 of SEQ ID NO: 2) binding stably to HLA molecules of the A2 type,
(24)TELQTTIHDI(33) (residues 24 to 33 of SEQ ID NO: 2) binding stably to HLA molecules of the A29 or B44 type,
(33)IILECVYCK(41) (residues 33 to 41 of SEQ ID NO: 2) binding stably to HLA molecules of the A11 type,
(35)LECVYCKQQL(44) (residues 35 to 44 of SEQ ID NO: 2) binding stably to HLA molecules of the A29 or B44 type,
(37)CVYCKQQL(44) (residues 37 to 44 of SEQ ID NO: 2) binding stably to HLA molecules of the B8 type,
(46)RREVYDFAFR(55) (residues 46 to 55 of SEQ ID NO: 2) binding stably to HLA molecules of the B27 type,
(49)VYDFAFRDL(57) (residues 49 to 57 of SEQ ID NO: 2) binding stably to HLA molecules of the A24 type,
(50)YDFAFRDL(57) (residues 50 to 57 of SEQ ID NO: 2) binding stably to HLA molecules of the A29, B44 type,
(52)FAFRDLCIV(60) (residues 52 to 60 of SEQ ID NO: 2) binding stably to HLA molecules of the A2, B35, B51 type,
(54)FRDLCIVYR(62) (residues 54 to 62 of SEQ ID NO: 2) binding stably to HLA molecules of the A3, A11 type,
(59)IVYRDGNPY(67) (residues 59 to 67 of SEQ ID NO: 2) binding stably to HLA molecules of the A3, A11 type,
(81)SEYRHYCY(88) (residues 81 to 88 of SEQ ID NO: 2) binding stably to HLA molecules of the A29, B44 type,
(87)CYSLYGTTL(95) (residues 87 to 95 of SEQ ID NO: 2) binding stably to HLA molecules of the A24 type,
(94)TLEQQYNK(101) (residues 94 to 101 of SEQ ID NO: 2) binding stably to HLA molecules of the A3, A11 type,
(95)LEQQYNKPL(103) (residues 95 to 103 of SEQ ID NO: 2) binding stably to HLA molecules of the A29, B44 type,
(101)KPLCDLLI(108) (residues 101 to 108 of SEQ ID NO: 2) binding stably to HLA molecules of the B7, B35, B51 type,
(118)CPEEKQRHL(126) (residues 118 to 126 of SEQ ID NO: 2) binding stably to HLA molecules of the B8, B18, B35, B51 type,
(119)PEEKQRHL(126) (residues 119 to 126 of SEQ ID NO: 2) binding stably to HLA molecules of the B44 type,
(127)DKKQRFHNI(135) (residues 127 to 135 of SEQ ID NO: 2) binding stably to HLA molecules of the B8 type,
(128)KKQRFHNIR(136) (residues 128 to 136 of SEQ ID NO: 2) binding stably to HLA molecules of the B27 type,
(130)QRFHNIRGRW(139) (residues 130 to 139 of SEQ ID NO: 2) binding stably to HLA molecules of the B27 type,
(131)RFHNIRGRW(139) (residues 131 to 139 of SEQ ID NO: 2) binding stably to HLA molecules of the A24 type.

The invention also relates to peptides or epitopes of the E7 protein of HPV selected from the following:

(3)GDTPTLHEY(11) (residues 3 to 11 of SEQ ID NO: 12) binding stably to HLA molecules of the B44 type,
(5)TPTLHEYML(13) (residues 5 to 13 of SEQ ID NO: 12) binding stably to HLA molecules of the B35 type,
(15)LQPETTDLY(23) (residues 15 to 23 of SEQ ID NO: 12) binding stably to HLA molecules of the B62 type, (16)QPETTDLYCY(25) (residues 16 to 25 of SEQ ID NO: 12) binding stably to HLA molecules of the A1, B18 type, (45)AEPDRAHY(52) (residues 45 to 52 of SEQ ID NO: 12) binding stably to HLA molecules of the A29, B44 type, (46)EPDRAHYNIV(55) (residues 46 to 55 of SEQ ID NO: 12) binding stably to HLA molecules of the B7 or B35 type, (53)NIVTFCCK(60) (residues 53 to 60 of SEQ ID NO: 12) binding stably to HLA molecules of the A3, A11 type, (79)LEDLLMGTL(87) (residues 79 to 87 of SEQ ID NO: 12) binding stably to HLA molecules of the A29, B44 type, (89)IVCPICSQK(97) (residues 89 to 97 of SEQ ID NO: 12) binding stably to HLA molecules of the A3, A11 type.

The invention also relates to peptide sequences derived from the above-mentioned peptides, said derived sequences, or the like, being as defined above in the framework of sequences derived from the polyepitopic protein fragments mentioned above.

The invention also has for its object the nucleotide sequences coding for peptides of the E6 or E7 proteins mentioned above, namely, the sequence delimited by the nucleotides located in positions 43 and 66 of the sequence SEQ ID NO: 1, coding for (15)RPRKLPQL(22) (residues 15 to 22 of SEQ ID NO: 2), the sequence delimited by the nucleotides located in positions 52 and 78 of the sequence SEQ ID NO: 1, coding for (18)KLPQLCTEL(26) (residues 18 to 26 of SEQ ID NO: 2), the sequence delimited by the nucleotides located in positions 55 and 78 of the sequence SEQ ID NO: 1, coding for (19)LPQLCTEL(26) (residues 19 to 26 of SEQ ID NO: 2), the sequence delimited by the nucleotides located in positions 61 and 90 of the sequence SEQ ID NO: 1, coding for (21)QLCTELQTTI(30) (residues 21 to 30 of SEQ ID NO: 2), the sequence delimited by the nucleotides located in positions 70 and 99 of the sequence SEQ ID NO: 1, coding for (24)TELQTTIHD(33) (residues 24 to 33 of SEQ ID NO: 2), the sequence delimited by the nucleotides located in positions 97 and 123 of the sequence SEQ ID NO: 1, coding for (33)IILECVYCK(41) (residues 33 to 41 of SEQ ID NO: 2), the sequence delimited by the nucleotides located in positions 103 and 132 of the sequence SEQ ID NO: 1, coding for (35)LECVYCKQQL(44) (residues 35 to 44 of SEQ ID NO: 2), the sequence delimited by the nucleotides located in positions 109 and 132 of the sequence SEQ ID NO: 1, coding for (37)CVYCKQQL(44) (residues 37 to 44 of SEQ ID NO: 2), the sequence delimited by the nucleotides located in positions 136 and 165 of the sequence SEQ ID NO: 1, coding for (46)RREVYDFAFR(55) (residues 46 to 55 of SEQ ID NO: 2), the sequence delimited by the nucleotides located in positions 145 and 171 of the sequence SEQ ID NO: 1, coding for (49)VFDFAFRDL(57) (residues 49 to 57 of SEQ ID NO: 2), the sequence delimited by the nucleotides located in positions 148 and 171 of the sequence SEQ ID NO: 1, coding for (50)YDFAFRDL(57) (residues 50 to 57 of SEQ ID NO: 2), the sequence delimited by the nucleotides located in positions 154 and 180 of the sequence SEQ ID NO: 1, coding for (52)FAFRDLCIV(60) (residues 52 to 60 of SEQ ID NO: 2), the sequence delimited by the nucleotides located in positions 160 and 186 of the sequence SEQ ID NO: 1, coding for (54)FRDLCIVYR(62) (residues 54 to 62 of SEQ ID NO: 2), the sequence delimited by the nucleotides located in positions 175 and 201 of the sequence SEQ ID NO: 1, coding for (59)IVYRDGNPY(67) (residues 59 to 67 of SEQ ID NO: 2), the sequence delimited by the nucleotides located in positions 241 and 264 of the sequence SEQ ID NO: 1, coding for (81)SEYRHYCY(88) (residues 81 to 88 of SEQ ID NO: 2), the sequence delimited by the nucleotides located in positions 259 and 285 of the sequence SEQ ID NO: 1, coding for (87)CYRLYGTTL(95) (residues 87 to 95 of SEQ ID NO: 2), the sequence delimited by the nucleotides located in positions 280 and 303 of the sequence SEQ ID NO: 1, coding for (94)TLEQQYNK(101) (residues 94 to 101 of SEQ ID NO: 2), the sequence delimited by the nucleotides located in positions 283 and 309 of the sequence SEQ ID NO: 1, coding for (95)LEQQYNKPL(103) (residues 95 to 103 of SEQ ID NO: 2), the sequence delimited by the nucleotides located in positions 301 and 324 of the sequence SEQ ID NO: 1, coding for (110)KPLCDLLI(108) (residues 101 to 108 of SEQ ID NO: 2), the sequence delimited by the nucleotides located in positions 352 and 378 of the sequence SEQ ID NO: 1, coding for (118)CPEEKQRHL(126) (residues 118 to 126 of SEQ ID NO: 2), the sequence delimited by the nucleotides located in positions 355 and 378 of the sequence SEQ ID NO: 1, coding for (119)PEEKQRHL(126) (residues 119 to 126 of SEQ ID NO: 2), the sequence delimited by the nucleotides located in positions 379 and 405 of the sequence SEQ ID NO: 1, coding for (127)DKKQRFHNI(135) (residues 127 to 135 of SEQ ID NO: 2), the sequence delimited by the nucleotides located in positions 382 and 408 of the sequence SEQ ID NO: 1, coding for (128)KKQRFHNIR(136) (residues 128 to 136 of SEQ ID NO: 2), the sequence delimited by the nucleotides located in positions 388 and 417 of the sequence SEQ ID NO: 1, coding for (130)QRFHNIRGRW(139) (residues 130 to 139 of SEQ ID NO: 2), the sequence delimited by the nucleotides located in positions 391 and 417 of the sequence SEQ ID NO: 1, coding for (131)RFHNIRGRW(139) (residues 131 to 139 of SEQ ID NO: 2), the sequence delimited by the nucleotides located in positions 7 and 33 of the sequence SEQ ID NO: 11, coding for (3)GDTPTLHEY(11) (residues 3 to 11 of SEQ ID NO: 12), the sequence delimited by the nucleotides located in positions 13 and 39 of the sequence SEQ ID NO: 11, coding for (5)TPTLHEYML(13) (residues 5 to 13 of SEQ ID NO: 12), the sequence delimited by the nucleotides located in positions 43 and 69 of the sequence SEQ ID NO: 11, coding for (15)LQPETTDLY(23) (residues 15 to 23 of SEQ ID NO: 12), the sequence delimited by the nucleotides located in positions 46 and 75 of the sequence SEQ ID NO: 11, coding for (16)QPETTDLYCY(25) (residues 16 to 25 of SEQ ID NO: 12), the sequence delimited by the nucleotides located in positions 133 and 153 of the sequence SEQ ID NO: 11, coding for (45)AEPDRAHY(52) (residues 45 to 52 of SEQ ID NO: 12), the sequence delimited by the nucleotides located in positions 136 and 165 of the sequence SEQ ID NO: 11, coding for (46)EPDRAHYNIV(55) (residues 46 to 55 of SEQ ID NO: 12), the sequence delimited by the nucleotides located in positions 157 and 180 of the sequence SEQ ID NO: 11, coding for (53)NIVTFCCK(60) (residues 53 to 60 of SEQ ID NO: 12), the sequence delimited by the nucleotides located in positions 235 and 261 of the sequence SEQ ID NO: 11, coding for (79)LEDLLMGTL(87) (residues 79 to 87 of SEQ ID NO: 12), the sequence delimited by the nucleotides located in positions 265 and 291 of the sequence SEQ ID NO: 11, coding for (89)IVCPICSQK(97) (residues 89 to 97 of SEQ ID NO: 12).

The invention also has for its object epitopes of the p53 protein selected from the following:

(102)TYQGSYGFRL(111) (residues 1 to 10 of SEQ ID NO: 19) binding stably to HLA molecules of the A24 type, (105)GSYGFRLGFL(114) (residues 4 to 13 of SEQ ID NO: 19) binding stably to HLA molecules of the B35 type, (106)SYGFRLGFL(114) (residues 5 to 13 of SEQ ID NO: 19) binding stably to HLA molecules of the A24 type, (118)TAKSVTCTY(126) (residues 17 to 25 of SEQ ID NO: 19) binding stably to HLA molecules of the B62 type, (125)TYSPALNKMF(134) (residues 24 to 33 of SEQ ID NO: 19) binding stably to HLA molecules of the A24 type, (152)PPGTRVRAM(160) (residues 4 to 12 of SEQ ID NO: 20) binding stably to HLA molecules of the B35 type, (155)TRVRAMAIYK(164) (residues 7 to 16 of SEQ ID NO: 20) binding stably to HLA molecules of the B27 type, (156)RVRAMAIY(163) (residues 8 to 15 of SEQ ID NO: 20) binding stably to HLA molecules of the B62 type, (162)IYKQSQHM(169) (residues 14 to 21 of SEQ ID NO: 20) binding stably to HLA molecules of the A24 type, (195)IRVEGNLRVEY(205) (residues 9 to 19 of SEQ ID NO: 21) binding stably to HLA molecules of the B27 type, (197)VEGNLRVEY(205) (residues 11 to 19 of SEQ ID NO: 21) binding stably to HLA molecules of the B44 type, (201)LRVEYLDDR(209) (residues 15 to 23 of SEQ ID NO: 21) binding stably to HLA molecules of the B27 type, (203)VEYLDDRNTF(212) (residues 17 to 26 of SEQ ID NO: 21) binding stably to HLA molecules of the B44 type, (204)EYLDDRNTF(212) (residues 18 to 26 of SEQ ID NO: 21) binding stably to HLA molecules of the A24 type, (211)TFRHSVVV(218) (residues 25 to 32 of SEQ ID NO: 21) binding stably to HLA molecules of the A24 type, (212)FRHSVVVPY(220) (residues 26 to 34 of SEQ ID NO: 21) binding stably to HLA molecules of the B27 type, (227)SDCTTIHYNY(236) (residues 2 to 11 of SEQ ID NO: 22) binding stably to HLA molecules of the B44 type, (235)NYMCNSSCM(243) (residues 10 to 18 of SEQ ID NO: 22) binding stably to HLA molecules of the A24 type, (249)RPILTIITL(257) (residues 2 to 10 of SEQ ID NO: 23) binding stably to HLA molecules of the B35 type, (257)LEDSSGNLL(265) (residues 10 to 18 of SEQ ID NO: 23) binding stably to HLA molecules of the B44 type, (263)NLLGRNSF(270) (residues 16 to 23 of SEQ ID NO: 23) binding stably to HLA molecules of the B62 type, (266)GRNSFEVR(273) (residues 19 to 26 of SEQ ID NO: 23) binding stably to HLA molecules of the B27 type, (272)VRVCACPGR(280) (residues 25 to 33 of SEQ ID NO: 23) binding stably to HLA molecules of the B27 type.

The invention also has for its object any process for the preparation of polyepitopic fragments, of single epitopes (above-mentioned peptides), or of derived sequences, by conventional peptide synthesis in liquid or solid phase.

As a modification, the polyepitopic fragments, single epitopes or derived peptide sequences, as defined above according to the invention, can be obtained in the form of recombinant polypeptides by transformation of suitable host cells as defined above with the help of vectors containing a recombinant nucleotide sequence as defined above according to the invention, and the recovery, as the case may be after purification, of the recombinant polypeptide coded by said nucleotide sequence and produced by the host cells mentioned above.

The invention claimed is:

1. A polyepitope of E7 protein from HPV, consisting of 23 amino acids delimited by the amino acids located in positions 3 and 25 of the peptide sequence of the E7 protein of HPV, wherein said polyepitope comprises peptide sequence SEQ ID NO: 14 as follows:

(3)GDTPTLHEYMLDLQPETTDLYCY(25)

and wherein said peptide sequence comprises 5 epitopes binding stably to at least one of 6 HLA molecules of the following types: A1, A2, B18, B35, B44 or B62, said epitopes being selected from the group consisting of:

(3)GDTPTLHEY(11) (residues 3 to 11 of SEQ ID NO: 12) binding stably to HLA molecules of the B44 type, (5)TPTLHEYML(13) (residues 5 to 13 of SEQ ID NO: 12) binding stably to HLA molecules of the B35 type, (11)YMLDLQPETT(20) (residues 11 to 20 of SEQ ID NO: 12) binding stably to HLA molecules of the A2 type, (15)LQPETTDL Y(23) (residues 15 to 23 of SEQ ID NO: 12) binding stably to HLA molecules of the B62 type, and (16)QPETTDLYCY(25) (residues 16 to 25 of SEQ ID NO: 12) binding stably to HLA molecules of the Al or B18 type.

2. A peptide sequence consisting of the amino acids of SEQ ID NO: 14, wherein said peptide sequence binds stably to at least one of 6 HLA molecules selected from the group consisting of A1, A2, B18, B35, B44 and B62.

* * * * *

SEQUENCE LISTING

<160> NUMBER OF SEQ ID NOS: 24

<210> SEQ ID NO 1
<211> LENGTH: 477
<212> TYPE: DNA
<213> ORGANISM: Human Papillomavirus

```
<220> FEATURE:
<221> NAME/KEY: CDS
<222> LOCATION: (1)..(477)

<400> SEQUENCE: 1 atg cac caa aag aga act gca atg ttt cag gac cca cag gag cga ccc    48
Met His Gln Lys Arg Thr Ala Met Phe Gln Asp Pro Gln Glu Arg Pro
 1               5                  10                  15 aga aag tta cca cag tta tgc aca gag ctg caa aca act ata cat gat    96
Arg Lys Leu Pro Gln Leu Cys Thr Glu Leu Gln Thr Thr Ile His Asp
            20                  25                  30 ata ata tta gaa tgt gtg tac tgc aag caa cag tta ctg cga cgt gag   144
Ile Ile Leu Glu Cys Val Tyr Cys Lys Gln Gln Leu Leu Arg Arg Glu
        35                  40                  45 gta tat gac ttt gct ttt cgg gat tta tgc ata gta tat aga gat ggg   192
Val Tyr Asp Phe Ala Phe Arg Asp Leu Cys Ile Val Tyr Arg Asp Gly
     50                  55                  60 aat cca tat gct gta tgt gat aaa tgt tta aag ttt tat tct aaa att   240
Asn Pro Tyr Ala Val Cys Asp Lys Cys Leu Lys Phe Tyr Ser Lys Ile
 65                  70                  75                  80 agt gag tat aga cat tat tgt tat agt ttg tat gga aca aca tta gaa   288
Ser Glu Tyr Arg His Tyr Cys Tyr Ser Leu Tyr Gly Thr Thr Leu Glu
                 85                  90                  95 cag caa tac aac aaa ccg ttg tgt gat ttg tta att agg tgt att aac   336
Gln Gln Tyr Asn Lys Pro Leu Cys Asp Leu Leu Ile Arg Cys Ile Asn
            100                 105                 110 tgt caa aag cca ctg tgt cct gaa gaa aag caa aga cat ctg gac aaa   384
Cys Gln Lys Pro Leu Cys Pro Glu Glu Lys Gln Arg His Leu Asp Lys
        115                 120                 125 aag caa aga ttc cat aat ata agg ggt cgg tgg acc ggt cga tgt atg   432
Lys Gln Arg Phe His Asn Ile Arg Gly Arg Trp Thr Gly Arg Cys Met
    130                 135                 140 tct tgt tgc aga tca tca aga aca cgt aga gaa acc cag ctg tga       477
Ser Cys Cys Arg Ser Ser Arg Thr Arg Arg Glu Thr Gln Leu
145                 150                 155

<210> SEQ ID NO 2
<211> LENGTH: 158
<212> TYPE: PRT
<213> ORGANISM: Human Papillomavirus

<400> SEQUENCE: 2

Met His Gln Lys Arg Thr Ala Met Phe Gln Asp Pro Gln Glu Arg Pro
 1               5                  10                  15

Arg Lys Leu Pro Gln Leu Cys Thr Glu Leu Gln Thr Thr Ile His Asp
            20                  25                  30

Ile Ile Leu Glu Cys Val Tyr Cys Lys Gln Gln Leu Leu Arg Arg Glu
        35                  40                  45

Val Tyr Asp Phe Ala Phe Arg Asp Leu Cys Ile Val Tyr Arg Asp Gly
     50                  55                  60

Asn Pro Tyr Ala Val Cys Asp Lys Cys Leu Lys Phe Tyr Ser Lys Ile
 65                  70                  75                  80

Ser Glu Tyr Arg His Tyr Cys Tyr Ser Leu Tyr Gly Thr Thr Leu Glu
                 85                  90                  95

Gln Gln Tyr Asn Lys Pro Leu Cys Asp Leu Leu Ile Arg Cys Ile Asn
            100                 105                 110

Cys Gln Lys Pro Leu Cys Pro Glu Glu Lys Gln Arg His Leu Asp Lys
        115                 120                 125

Lys Gln Arg Phe His Asn Ile Arg Gly Arg Trp Thr Gly Arg Cys Met
```

```
                130                 135                 140
Ser Cys Cys Arg Ser Ser Arg Thr Arg Arg Glu Thr Gln Leu
145                 150                 155

<210> SEQ ID NO 3
<211> LENGTH: 90
<212> TYPE: DNA
<213> ORGANISM: Artificial Sequence
<220> FEATURE:
<223> OTHER INFORMATION: Description of the Artificial Sequence:
      fragment of the sequence coding for E6 of HPV and corresponding
      peptide sequence
<220> FEATURE:
<221> NAME/KEY: CDS
<222> LOCATION: (1)..(90)

<400> SEQUENCE: 3 cga ccc aga aag tta cca cag tta tgc aca gag ctg caa aca act ata        48
Arg Pro Arg Lys Leu Pro Gln Leu Cys Thr Glu Leu Gln Thr Thr Ile
  1               5                  10                  15 cat gat ata ata tta gaa tgt gtg tac tgc aag caa cag tta              90
His Asp Ile Ile Leu Glu Cys Val Tyr Cys Lys Gln Gln Leu
             20                  25                  30

<210> SEQ ID NO 4
<211> LENGTH: 30
<212> TYPE: PRT
<213> ORGANISM: Artificial Sequence
<220> FEATURE:
<223> OTHER INFORMATION: Description of the Artificial Sequence: Peptide
      fragment for E6 of HPV

<400> SEQUENCE: 4

Arg Pro Arg Lys Leu Pro Gln Leu Cys Thr Glu Leu Gln Thr Thr Ile
  1               5                  10                  15

His Asp Ile Ile Leu Glu Cys Val Tyr Cys Lys Gln Gln Leu
             20                  25                  30

<210> SEQ ID NO 5
<211> LENGTH: 66
<212> TYPE: DNA
<213> ORGANISM: Artificial Sequence
<220> FEATURE:
<223> OTHER INFORMATION: Description of the Artificial Sequence:
      fragment of the sequence coding for E6 of HPV and corresponding
      peptide sequence
<220> FEATURE:
<221> NAME/KEY: CDS
<222> LOCATION: (1)..(66)

<400> SEQUENCE: 5 cga cgt gag gta tat gac ttt gct ttt cgg gat tta tgc ata gta tat       48
Arg Arg Glu Val Tyr Asp Phe Ala Phe Arg Asp Leu Cys Ile Val Tyr
  1               5                  10                  15 aga gat ggg aat cca tat                                               66
Arg Asp Gly Asn Pro Tyr
             20

<210> SEQ ID NO 6
<211> LENGTH: 22
<212> TYPE: PRT
<213> ORGANISM: Artificial Sequence
<220> FEATURE:
<223> OTHER INFORMATION: Description of the Artificial Sequence: Peptide
      fragment for E6 of HPV

<400> SEQUENCE: 6
```

-continued

```
Arg Arg Glu Val Tyr Asp Phe Ala Phe Arg Asp Leu Cys Ile Val Tyr
 1               5                  10                  15

Arg Asp Gly Asn Pro Tyr
            20

<210> SEQ ID NO 7
<211> LENGTH: 87
<212> TYPE: DNA
<213> ORGANISM: Artificial Sequence
<220> FEATURE:
<223> OTHER INFORMATION: Description of the Artificial Sequence:
      fragment of the sequence coding for E6 of HPV and corresponding
      peptide sequence
<220> FEATURE:
<221> NAME/KEY: CDS
<222> LOCATION: (1)..(87)

<400> SEQUENCE: 7 att agt gag tat aga cat tat tgt tat agt ttg tat gga aca aca tta         48
Ile Ser Glu Tyr Arg His Tyr Cys Tyr Ser Leu Tyr Gly Thr Thr Leu
 1               5                  10                  15 gaa cag caa tac aac aaa ccg ttg tgt gat ttg tta att                     87
Glu Gln Gln Tyr Asn Lys Pro Leu Cys Asp Leu Leu Ile
            20                  25

<210> SEQ ID NO 8
<211> LENGTH: 29
<212> TYPE: PRT
<213> ORGANISM: Artificial Sequence
<220> FEATURE:
<223> OTHER INFORMATION: Description of the Artificial Sequence: Peptide
      fragment for E6 of HPV

<400> SEQUENCE: 8

Ile Ser Glu Tyr Arg His Tyr Cys Tyr Ser Leu Tyr Gly Thr Thr Leu
 1               5                  10                  15

Glu Gln Gln Tyr Asn Lys Pro Leu Cys Asp Leu Leu Ile
            20                  25

<210> SEQ ID NO 9
<211> LENGTH: 66
<212> TYPE: DNA
<213> ORGANISM: Artificial Sequence
<220> FEATURE:
<223> OTHER INFORMATION: Description of the Artificial Sequence:
      fragment of the sequence coding for E6 of HPV and corresponding
      peptide sequence
<220> FEATURE:
<221> NAME/KEY: CDS
<222> LOCATION: (1)..(66)

<400> SEQUENCE: 9 tgt cct gaa gaa aag caa aga cat ctg gac aaa aag caa aga ttc cat         48
Cys Pro Glu Glu Lys Gln Arg His Leu Asp Lys Lys Gln Arg Phe His
 1               5                  10                  15 aat ata agg ggt cgg tgg                                                 66
Asn Ile Arg Gly Arg Trp
            20

<210> SEQ ID NO 10
<211> LENGTH: 22
<212> TYPE: PRT
<213> ORGANISM: Artificial Sequence
<220> FEATURE:
<223> OTHER INFORMATION: Description of the Artificial Sequence: Peptide
      fragment for E6 of HPV

<400> SEQUENCE: 10
```

Cys Pro Glu Glu Lys Gln Arg His Leu Asp Lys Lys Gln Arg Phe His
1               5                   10                  15

Asn Ile Arg Gly Arg Trp
            20

<210> SEQ ID NO 11
<211> LENGTH: 297
<212> TYPE: DNA
<213> ORGANISM: Human Papillomavirus
<220> FEATURE:
<221> NAME/KEY: CDS
<222> LOCATION: (1)..(297)

<400> SEQUENCE: 11

```
atg cat gga gat aca cct aca ttg cat gaa tat atg tta gat ttg caa      48
Met His Gly Asp Thr Pro Thr Leu His Glu Tyr Met Leu Asp Leu Gln
1               5                   10                  15 cca gag aca act gat ctc tac tgt tat gag caa tta aat gac agc tca      96
Pro Glu Thr Thr Asp Leu Tyr Cys Tyr Glu Gln Leu Asn Asp Ser Ser
            20                  25                  30 gag gag gag gat gaa ata gat ggt cca gct gga caa gca gaa ccg gac     144
Glu Glu Glu Asp Glu Ile Asp Gly Pro Ala Gly Gln Ala Glu Pro Asp
        35                  40                  45 aga gcc cat tac aat att gta acc ttt tgt tgc aag tgt gac tct acg     192
Arg Ala His Tyr Asn Ile Val Thr Phe Cys Cys Lys Cys Asp Ser Thr
    50                  55                  60 ctt cgg ttg tgc gta caa agc aca cac gta gac att cgt act ttg gaa     240
Leu Arg Leu Cys Val Gln Ser Thr His Val Asp Ile Arg Thr Leu Glu
65                  70                  75                  80 gac ctg tta atg ggc aca cta gga att gtg tgc ccc atc tgt tct cag     288
Asp Leu Leu Met Gly Thr Leu Gly Ile Val Cys Pro Ile Cys Ser Gln
                85                  90                  95 aaa cca taa                                                          297
Lys Pro
```

<210> SEQ ID NO 12
<211> LENGTH: 98
<212> TYPE: PRT
<213> ORGANISM: Human Papillomavirus

<400> SEQUENCE: 12

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
            20                  25                  30

Glu Glu Glu Asp Glu Ile Asp Gly Pro Ala Gly Gln Ala Glu Pro Asp
        35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95

Lys Pro

<210> SEQ ID NO 13
<211> LENGTH: 69
<212> TYPE: DNA
<213> ORGANISM: Artificial Sequence
<220> FEATURE:

```
<223> OTHER INFORMATION: Description of the Artificial Sequence:
      fragment of the sequence coding for E7 of HPV and corresponding
      peptide sequence
<220> FEATURE:
<221> NAME/KEY: CDS
<222> LOCATION: (1)..(69)

<400> SEQUENCE: 13 gga gat aca cct aca ttg cat gaa tat atg tta gat ttg caa cca gag      48
Gly Asp Thr Pro Thr Leu His Glu Tyr Met Leu Asp Leu Gln Pro Glu
 1               5                  10                  15 aca act gat ctc tac tgt tat                                          69
Thr Thr Asp Leu Tyr Cys Tyr
            20

<210> SEQ ID NO 14
<211> LENGTH: 23
<212> TYPE: PRT
<213> ORGANISM: Artificial Sequence
<220> FEATURE:
<223> OTHER INFORMATION: Description of the Artificial Sequence: Peptide
      fragment for E7 of HPV

<400> SEQUENCE: 14

Gly Asp Thr Pro Thr Leu His Glu Tyr Met Leu Asp Leu Gln Pro Glu
 1               5                  10                  15

Thr Thr Asp Leu Tyr Cys Tyr
            20

<210> SEQ ID NO 15
<211> LENGTH: 51
<212> TYPE: DNA
<213> ORGANISM: Artificial Sequence
<220> FEATURE:
<223> OTHER INFORMATION: Description of the Artificial Sequence:
      fragment of the sequence coding for E7 of HPV and corresponding
      peptide sequence
<220> FEATURE:
<221> NAME/KEY: CDS
<222> LOCATION: (1)..(51)

<400> SEQUENCE: 15 caa gca gaa ccg gac aga gcc cat tac aat att gta acc ttt tgt tgc      48
Gln Ala Glu Pro Asp Arg Ala His Tyr Asn Ile Val Thr Phe Cys Cys
 1               5                  10                  15 aag                                                                  51
Lys

<210> SEQ ID NO 16
<211> LENGTH: 17
<212> TYPE: PRT
<213> ORGANISM: Artificial Sequence
<220> FEATURE:
<223> OTHER INFORMATION: Description of the Artificial Sequence: Peptide
      fragment for E7 of HPV

<400> SEQUENCE: 16

Gln Ala Glu Pro Asp Arg Ala His Tyr Asn Ile Val Thr Phe Cys Cys
 1               5                  10                  15

Lys

<210> SEQ ID NO 17
<211> LENGTH: 57
<212> TYPE: DNA
<213> ORGANISM: Artificial Sequence
<220> FEATURE:
<223> OTHER INFORMATION: Description of the Artificial Sequence:
```

```
        fragment of the sequence coding for E7 of HPV and corresponding
        peptide sequence
<220> FEATURE:
<221> NAME/KEY: CDS
<222> LOCATION: (1)..(57)

<400> SEQUENCE: 17 ttg gaa gac ctg tta atg ggc aca cta gga att gtg tgc ccc atc tgt        48
Leu Glu Asp Leu Leu Met Gly Thr Leu Gly Ile Val Cys Pro Ile Cys
 1               5                  10                  15 tct cag aaa                                                              57
Ser Gln Lys <210> SEQ ID NO 18
<211> LENGTH: 19
<212> TYPE: PRT
<213> ORGANISM: Artificial Sequence
<220> FEATURE:
<223> OTHER INFORMATION: Description of the Artificial Sequence: Peptide
        fragment for E7 of HPV

<400> SEQUENCE: 18

Leu Glu Asp Leu Leu Met Gly Thr Leu Gly Ile Val Cys Pro Ile Cys
 1               5                  10                  15

Ser Gln Lys

<210> SEQ ID NO 19
<211> LENGTH: 36
<212> TYPE: PRT
<213> ORGANISM: Homo sapiens

<400> SEQUENCE: 19

Thr Tyr Gln Gly Ser Tyr Gly Phe Arg Leu Gly Phe Leu His Ser Gly
 1               5                  10                  15

Thr Ala Lys Ser Val Thr Cys Thr Tyr Ser Pro Ala Leu Asn Lys Met
                20                  25                  30

Phe Cys Gln Leu
            35

<210> SEQ ID NO 20
<211> LENGTH: 21
<212> TYPE: PRT
<213> ORGANISM: Homo sapiens

<400> SEQUENCE: 20

Ser Thr Pro Pro Pro Gly Thr Arg Val Arg Ala Met Ala Ile Tyr Lys
 1               5                  10                  15

Gln Ser Gln His Met
            20

<210> SEQ ID NO 21
<211> LENGTH: 34
<212> TYPE: PRT
<213> ORGANISM: Homo sapiens

<400> SEQUENCE: 21

Gly Leu Ala Pro Pro Gln His Leu Ile Arg Val Glu Gly Asn Leu Arg
 1               5                  10                  15

Val Glu Tyr Leu Asp Asp Arg Asn Thr Phe Arg His Ser Val Val Val
                20                  25                  30

Pro Tyr
```

-continued

```
<210> SEQ ID NO 22
<211> LENGTH: 18
<212> TYPE: PRT
<213> ORGANISM: Homo sapiens

<400> SEQUENCE: 22

Gly Ser Asp Cys Thr Thr Ile His Tyr Asn Tyr Met Cys Asn Ser Ser
  1               5                  10                  15

Cys Met

<210> SEQ ID NO 23
<211> LENGTH: 33
<212> TYPE: PRT
<213> ORGANISM: Homo sapiens

<400> SEQUENCE: 23

Arg Arg Pro Ile Leu Thr Ile Ile Thr Leu Glu Asp Ser Ser Gly Asn
  1               5                  10                  15

Leu Leu Gly Arg Asn Ser Phe Glu Val Arg Val Cys Ala Cys Pro Gly
             20                  25                  30

Arg

<210> SEQ ID NO 24
<211> LENGTH: 17
<212> TYPE: PRT
<213> ORGANISM: Clostridium tetani

<400> SEQUENCE: 24

Gln Tyr Ile Lys Ala Asn Ser Lys Phe Ile Gly Ile Thr Glu Leu Lys
  1               5                  10                  15

Lys
```